United States Patent [19]
Silberg

[11] Patent Number: 6,039,048
[45] Date of Patent: *Mar. 21, 2000

[54] EXTERNAL ULTRASOUND TREATMENT OF CONNECTIVE TISSUE

[76] Inventor: Barry Silberg, 1111 Sonoma Ave., Ste 210, Santa Rosa, Calif. 95405

[*] Notice: This patent is subject to a terminal disclaimer.

[21] Appl. No.: 09/057,163

[22] Filed: Apr. 8, 1998

Related U.S. Application Data

[63] Continuation of application No. 08/842,873, Mar. 23, 1999, Pat. No. 5,884,631.

[51] Int. Cl.[7] .................................................. A61B 19/00
[52] U.S. Cl. ................................. 128/898; 604/22
[58] Field of Search ................... 604/36, 19, 22, 604/28, 49, 73, 119, 174, 902, 905; 128/898

[56] References Cited

U.S. PATENT DOCUMENTS

| | | | |
|---|---|---|---|
| 4,886,491 | 12/1989 | Parisi et al. | 604/22 |
| 5,052,999 | 10/1991 | Klein | 604/19 |
| 5,419,761 | 5/1995 | Narayanan et al. | 604/22 |
| 5,447,493 | 9/1995 | Blugerman et al. | 604/35 |
| 5,472,416 | 12/1995 | Blugerman et al. | 604/28 |
| 5,527,273 | 6/1996 | Manna et al. | 604/22 |
| 5,569,178 | 10/1996 | Henley | 604/22 |
| 5,651,773 | 7/1997 | Perry et al. | 604/174 |

OTHER PUBLICATIONS

Weber, "Liposuction Information" URL: http://www.lipoinfo.com, 1996.
Hudson, "Ultrsonic Liposuction" E–STHETICS internet site, URL: http://www.phudson.com/UAL/UALtext.htm, 1998.

*Primary Examiner*—Mickey Yu
*Assistant Examiner*—Kelly O'Hara
*Attorney, Agent, or Firm*—Mark E. Ogram P.C.

[57] ABSTRACT

Using an external ultrasonic generator, ultrasonic waves are transmitted through the skin to the cells and tumescent solution. The ultrasonic waves disrupt the connective tissue between the cells.

12 Claims, 4 Drawing Sheets

EXTERNAL ULTRASOUND TREATMENT OF CONNECTIVE TISSUE

BACKGROUND OF THE INVENTION

This is a continuation of U.S. patent application Ser. No. 08/842,873, filed Apr. 17, 1997, now U.S. Pat. No. 5,884,631 and entitled "Improved Body Contouring Technique and Apparatus" now U.S. Pat. No. 5,884,631, issued on Mar. 23, 1999.

This invention relates generally to surgical techniques and apparatus, and more particularly to techniques and apparatus used to remove fat cells from a patient.

Often, regardless of the amount of exercise or dieting that a patient endures, certain areas of fat are not diminished. When this happens, the patient becomes increasingly frustrated and despondent about their ability to obtain the body shape that they desire.

Because of this, the most common cosmetic surgery performed today is liposuction. This technique is often referred to as "body contouring" as the actual contours of the body are manipulated to obtain the aesthetic qualities sought by the patient.

Liposuction generally involves using a general anesthetic on the patient during the procedure. An incision near the site to be contoured is made, and a cannula is inserted into the fatty area. Using suction to remove fat cells from the site, the surgeon repeatedly moves the cannula to break the connective tissue holding the fat cells. The fat cells are then "sucked" or drawn from the site.

While this procedure accomplishes its task, it is a highly invasive procedure which can cause significant bleeding and discomfort for the patient during recuperation.

Physical recuperation from the procedure of liposuction is relatively short; but, due to the naturally occurring bruising, a significant period must elapse before the patient is "presentable".

It is clear that there is a need for a less invasive and less traumatic technique for the removal of unwanted fat from a patient.

SUMMARY OF THE INVENTION

The present invention is a technique for body contouring or the removal of undesired fat cells or soft tissue in which a wetting solution such as a tumescent solution is injected among the fat cells or soft tissue.

While the present invention discusses the infusion of a tumescent solution, the invention is not intended to be so limited as a variety of other medicinal liquids which act as wetting solutions are also contemplated such as a saline solution. Those of ordinary skill in the art recognize such liquids.

Tumescent solutions are specially adapted to provide for the application of local anesthesia and are well known in the art. Tumescent solutions employ a variety of medicated solutions. The preferred solution uses 1000 milliliters of normal saline with 2% lidocaine, 30 ml. (600 mg) of epinephrine, and one mole (12.5 ml or 12.5 mg.) of sodium bicarbonate. These additives are commercially available.

To improve the lidocaine action and to reduce infiltration suffering, the preferred apparatus applies the tumescent solution at body temperature. Heating of the solution is accomplished using a variety of techniques such as use of a microwave oven, other heating techniques are well known in the art and are also acceptable. In some applications, the tumescent solution is not heated.

In some applications, the tumescent solution is chilled prior to injection. The chilled solution reduces the local temperature within the patient to counteract the natural heating caused by ultrasonic waves.

The tumescent solution is inserted using a syringe. Pressure, provided by a plunger of the syringe, forces the tumescent solution through the openings in the distal end of the needle.

The preferred method of applying the tumescent solution is through the use of an infusion pump which draws the solution from a reservoir and infuses the solution under pressure.

In one embodiment of the invention, little or no wetting liquid is used. Rather, the frequency of the ultrasonic wave is chosen, based on the specific gravity of the targeted soft tissue, to affect only the targeted fat cells or soft tissue.

After suspension, the fat cells are vibrated in the ultrasonic range. Ultrasonic in this context includes all signals which are above human hearing or above about 20,000 hertz.

The preferred technique for applying the ultrasonic vibrations is through the use of an ultrasonic emitter which is placed on the skin proximate to the fat cells. The ultrasonic emitter generates ultrasonic waves which are communicated through the skin to vibrate the tumescent solution and fat cells at the desired frequency. The transmitted waves cause a vibration within the fat cells which is in the ultrasonic range.

Preferably, the temperature of the site is monitored to prevent excess heat buildup. Should the ultrasonic vibration cause too much heat, the surrounding tissue and skin can be inadvertently damaged.

This vibration damages the cells and also assists in disrupting the connective tissue between the cells. To this end, the vibration is continued until the desired affect is accomplished.

The now damaged or disconnected fat cells are then removed either through the body's natural actions in "sloughing" dead or damaged cells or by traditional liposuction techniques which suction the cells from the site.

While the body has the ability to naturally "discharge" damaged cells, this task places added demands upon the body's liver. In one embodiment of the invention, antibiotics and other medicines are administered to the patient either before or after the fat cells have been damaged to assist the liver in its task of cell removal.

In another technique, the cells are removed through the use of suction which is applied using a customary liposuction apparatus. After using the present invention's ultrasonic breakage of the connective tissue, the liposuction technique operates much more smoothly as the ultrasonic vibration has disrupted the connective tissue permitting the fat cells to "float" and to be easily removed.

In one embodiment of the invention, the ultrasonic vibration and the suction are performed simultaneously. To facilitate this procedure, a hand-held probe is used which aligns the ultrasonic generator with the tip of the suction probe.

Due to the tumescent solution, bleeding within the site is minimized. Because of this, the chance of, and amount of, bruising is greatly reduced; thereby allowing the patient to obtain a "presentable" appearance almost immediately after the surgical technique. Also, the tumescent solution reduces the patient's discomfort.

The invention, together with various embodiments thereof, will be explained in more detail by the accompanying drawings and the following description.

DRAWINGS IN BRIEF

DRAWINGS IN DETAIL

Figure 1:
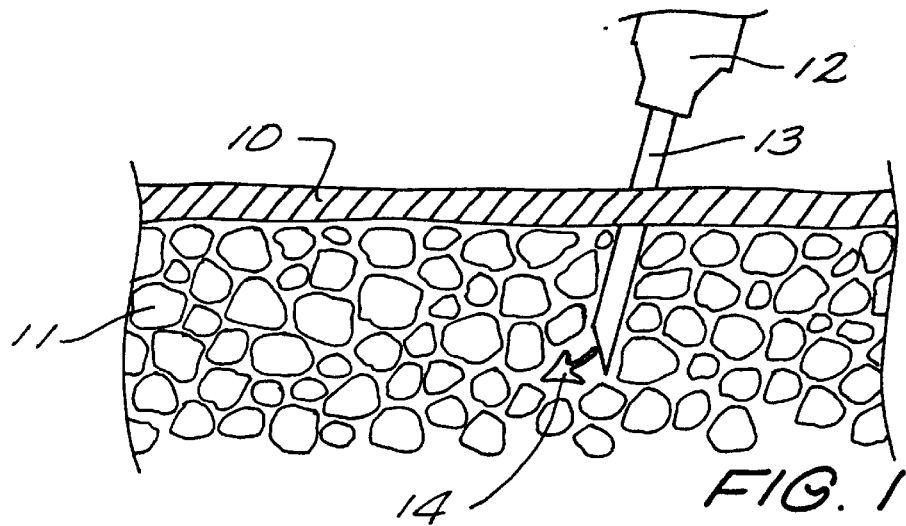
FIG. 1 illustrates the injection of the preferred tumescent solution among the fat cells.

FIG. 1 illustrates the injection of the preferred tumescent solution among the fat cells.

Fat cells 11 are, in this illustration, located below skin layer 10. Needle 13, attached to infusion pump handle 12, is inserted through skin layer 10 allowing tumescent solution, as illustrated by arrow 14, to be injected among fat cells 11.

In the present discussion, fat cells are used for examples of soft tissue which are addressed by the present invention. The invention though is not so limited as the invention is readily applied to the removal of a wide assortment of soft tissue through control of the frequency of the ultrasonic generator. Those of ordinary skill in the art readily recognize the computations required, and the adjustments which are to be made, to match the ultrasonic wave generator's frequency to the specific gravity of the targeted soft tissue.

While the preferred embodiment uses a tumescent solution, the invention is not so limited as any liquid, such as saline, assists in forming a suspension of fat cells 11 for the later steps. The tumescent solution acts as a wetting agent.

The choice of a tumescent solution in the preferred embodiment capitalizes upon the solution's application of local anesthesia to reduce patient discomfort. The preferred solution uses 1000 milliliters of normal saline with 2% lidocaine, 30 ml. (600 mg) of epinephrine, and one mole (12.5 ml or 12.5 mg.) of sodium bicarbonate. These additives are commercially available.

Figure 2:
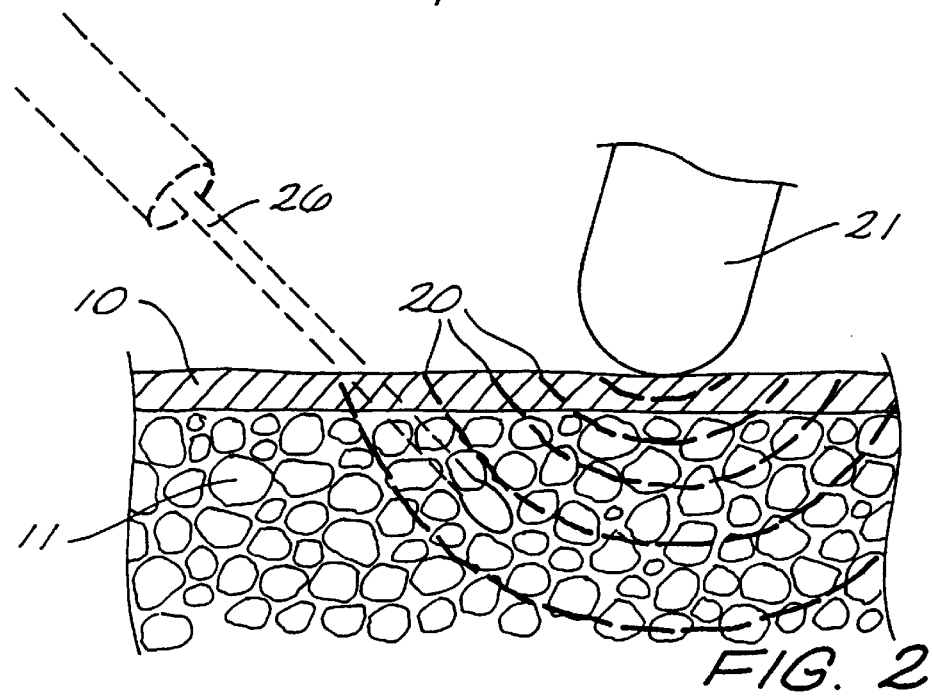
FIG. 2 illustrates the preferred technique for applying the ultrasonic vibration to the fat cells and the tumescent solution.

FIG. 2 illustrates the preferred technique used for applying ultrasonic vibration to the fat cells and the tumescent solution.

Ultrasonic vibrations are passed as waves 20 through the skin by applicator 21. This technique, passing the ultrasonic waves through the skin, significantly reduces the trauma to the patient as the use of invasive techniques is minimized.

Ultrasonic waves 20 vibrate the fat cells 11 and tumescent solution. This vibration causes the connective tissue between the cells to break and also tends to damage the fat cells themselves.

In one embodiment, temperature probe 26 is inserted so that the temperature of the fat cells are monitored. This in-situ monitoring assures the surgeon that the ultrasonic vibrations being applied do not generate excessive heat within the fat cells which can damage surrounding tissue.

An alternative approach to this technique is to monitor the temperature at the skin layer as most fatty sites which are to be removed are near the skin surface.

Figure 3A:
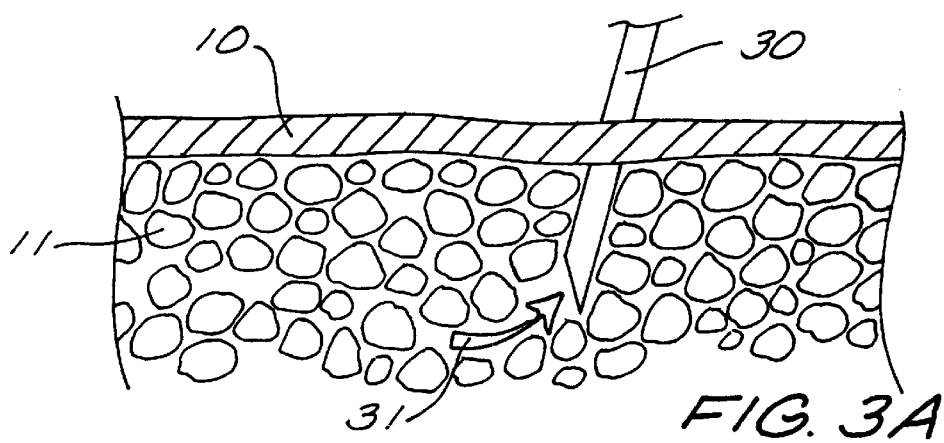
FIGS. 3A and 3B illustrate alternative embodiments for the withdrawal of the fat cells.
Figure 3B:
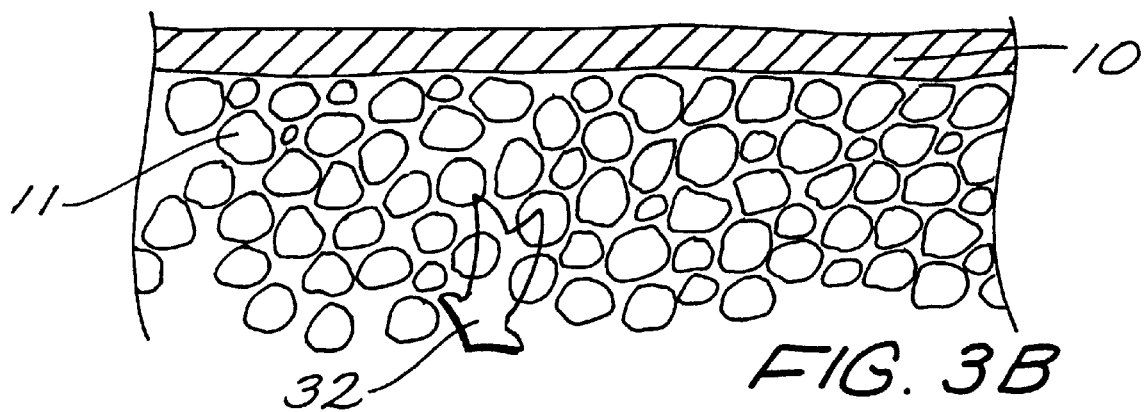

FIGS. 3A and 3B illustrate alternative embodiments for the withdrawal of the fat cells.

In FIG. 3A, the ultrasonic waves have been applied to the fat cells 11 and tumescent solution. The connective tissue between the fat cells has been either broken or significantly weakened.

Needle 30 is inserted through the skin layer 10 so that the tip of the needle is positioned within the fat cells. Suction is then applied, as illustrated by arrow 31, to draw the fat cells out of the patient's body.

Since the connective tissue is broken or weakened, this suction is much more effective and creates less trauma since the fat cells are substantially "isolated".

In FIG. 3B, the preferred method of withdrawing the fat cells is shown. In this embodiment, fat cells 11 have been damaged and their connective tissue has been either broken or weakened by the ultrasonic waves. Because of this, the patient's own immune system removes the fat cells and discharges them 32.

This is accomplished by the patient's immune system which constantly "cleanses" the body of damaged cells. These damaged fat cells are filtered from the blood by the liver. In some applications, when a large pocket of damaged fat cells are to be removed by the immune system, the body's immune system is bolstered by the addition of an antibiotic. Those of ordinary skill in the art readily recognize a variety of medicines which can be used in this context.

Figure 4A:
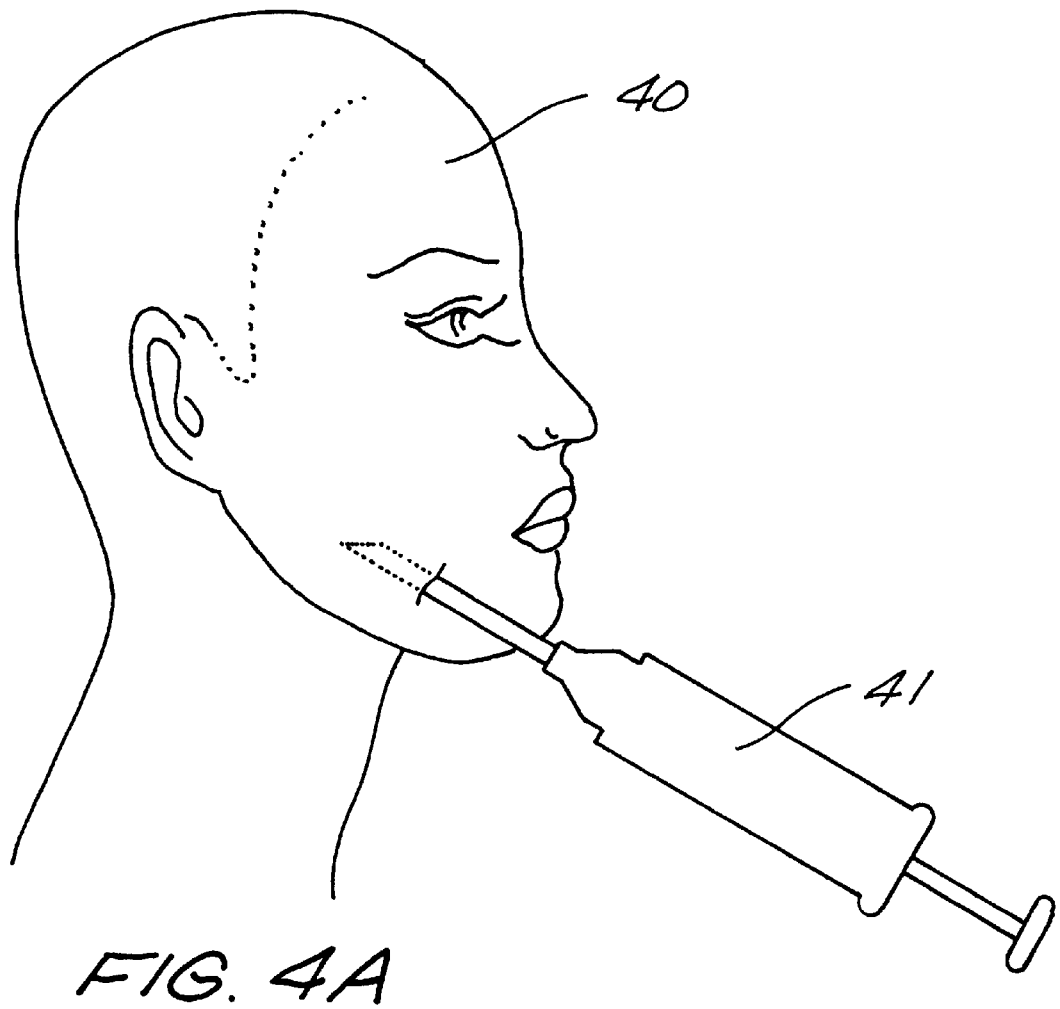
FIGS. 4A and 4B are side views of a patient having fat along a jaw-line treated using the present invention's technique.
Figure 4B:
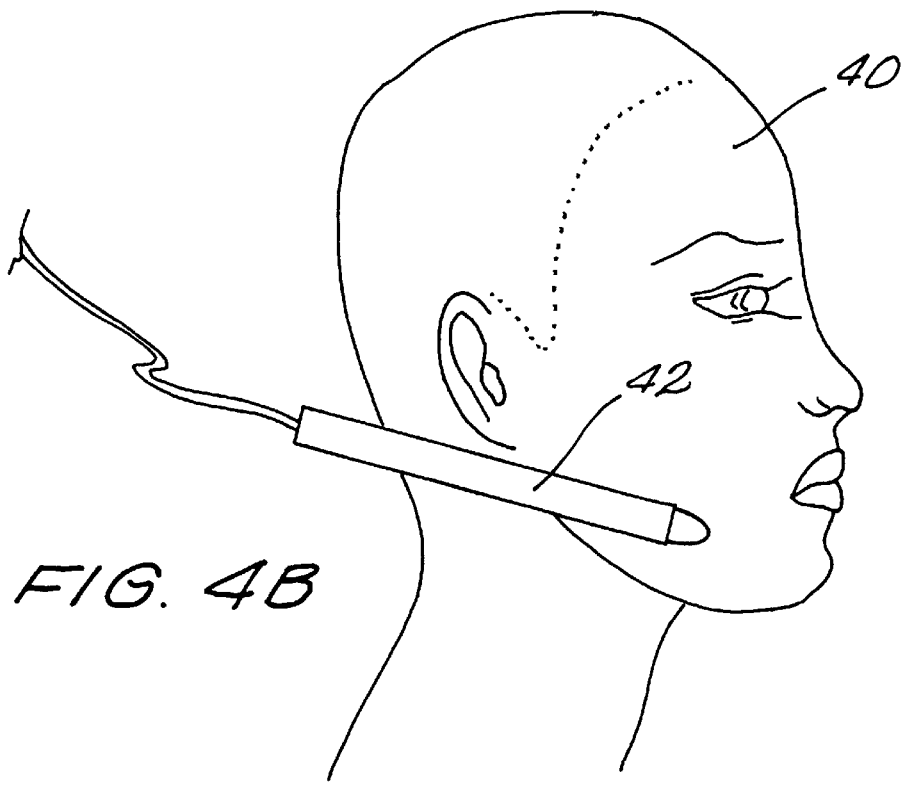

FIGS. 4A and 4B are side views of a patient having fat along a jaw-line treated using the present invention's technique.

The initial step, illustrated in FIG. 4A, is to have a tumescent solution injected into the chosen site of patient 40 using syringe 41.

Once the tumescent solution is in place, the ultrasonic generator 42 is passed over the skin to send ultrasonic waves into the chosen site (FIG. 4B). This is done for sufficient time so that the connective tissue is broken or weakened to the satisfaction of the surgeon.

In this illustration, the patient is then able to leave without any liposuction being performed. The now disconnected fat cells are absorbed by the body. This removal of the fat cells creates a natural removal of the fat cells so that the desired contouring of the body is achieved.

Figure 5:
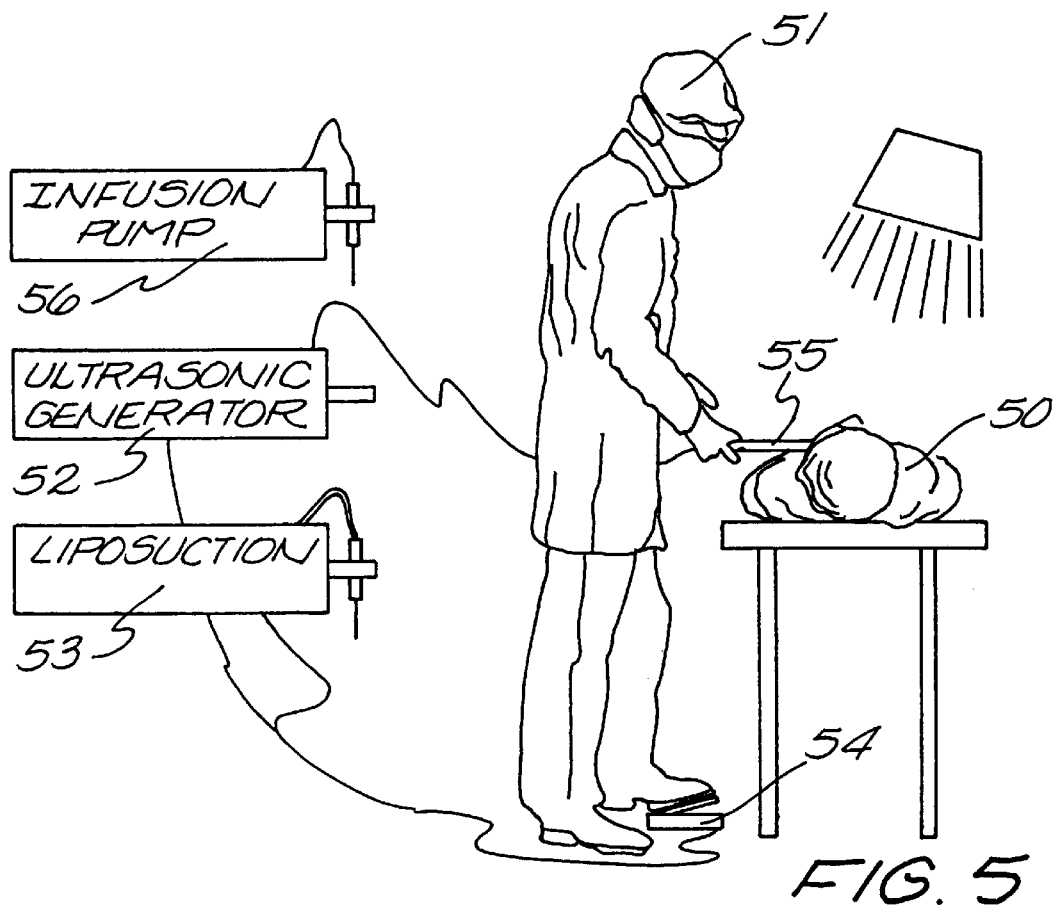
FIG. 5 illustrates a surgeon applying the technique of this invention to a patient.

FIG. 5 illustrates a surgeon applying the technique of this invention to a patient.

Patient 50 is disposed so that surgeon has easy access to the site to be contoured. In this illustration, the tumescent solution has already been administered via infusion pump 56, and the surgeon has activated, via foot control 54, ultrasonic generator 52 which applies the chosen vibrations to the site by surgeon 51 using hand unit 55.

When the proper amount of ultrasonic vibration has been performed, surgeon 51 uses liposuction apparatus 53, again controlled by foot control 54, to remove the affected fat cells.

Figure 6:
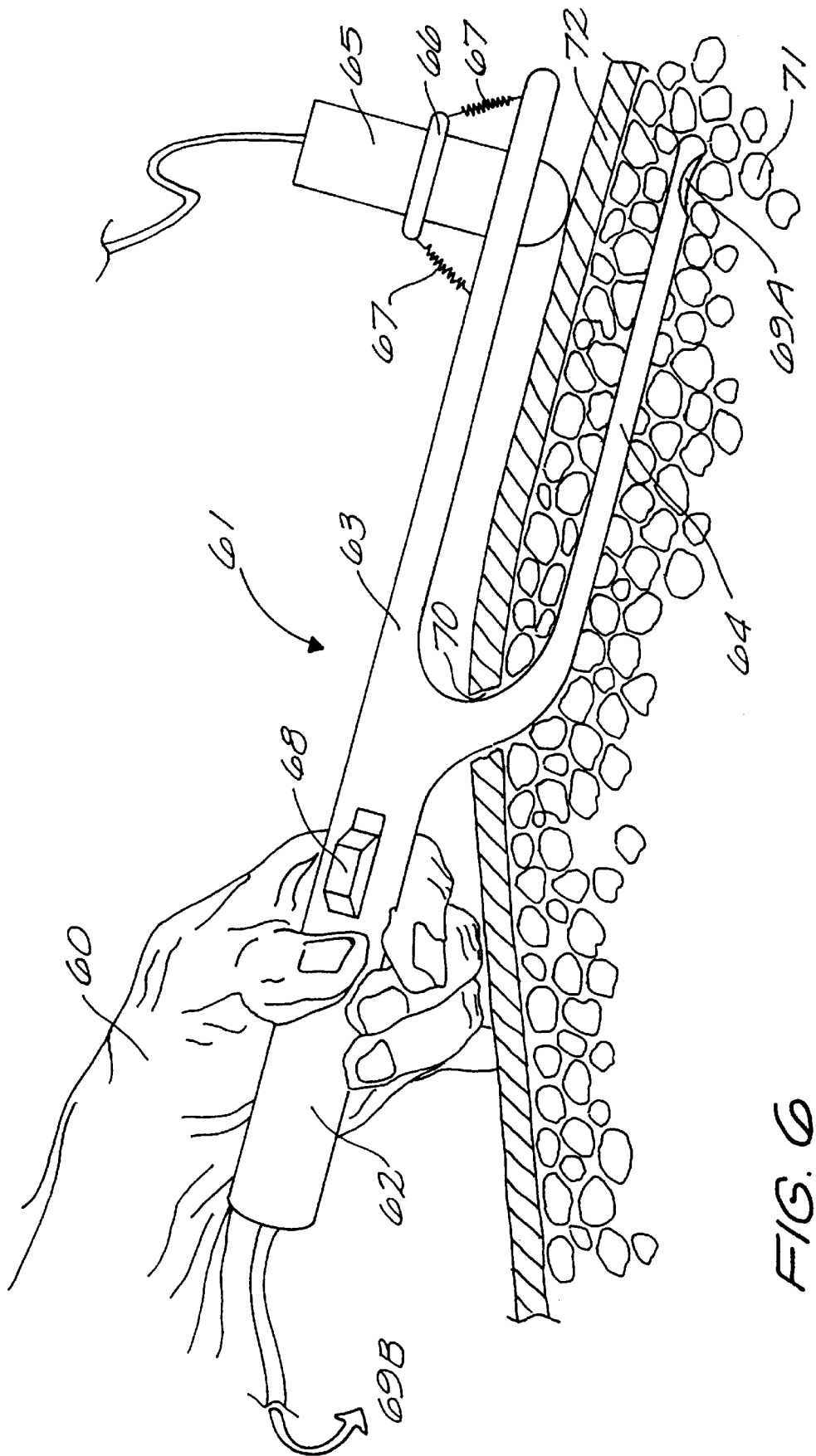
FIG. 6 illustrates an embodiment of the invention in which the ultrasonic waves are passed through the skin simultaneously with the application of the liposuction procedure.

FIG. 6 illustrates an embodiment of the invention in which the ultrasonic waves are passed through the skin simultaneously with the application of the liposuction procedure.

Surgeon 60 grasps handle 62 of instrument 61. Instrument 61 includes a suction cannula 64 which is inserted through incision 70 so that a tip of suction cannula 64 is positioned within the fat cells 71 to be removed.

Instrument 61 also includes positioning frame 63 which accepts ultrasonic generator 65. Ultrasonic generator 65 is pressed against skin 72 over the tip of suction cannula 64 using harness 66 and springs 67. This assures the effective passage of the ultrasonic waves through skin 72 to disrupt and damage the underlying fat cells 71.

Fat cells 71 are withdrawn from the site, as indicated by arrow 69A, and placed in a reservoir (not shown) as indicated by arrow 69B.

Switch 68 permits surgeon 60 to activate the mechanism.

This apparatus permits the surgeon to simultaneously pass ultrasonic waves into the patient and withdraw the fat cells.

It is clear that the present invention creates a highly improved method and apparatus for the removal of unwanted fat and soft tissue from a patient.

What is claimed is:

1. A technique comprising the steps of:
    a) injecting a quantity of tumescent solution into a surgical site; and,
    b) vibrating, through skin of a patient, said tumescent solution in the ultrasonic range sufficient to loosen intercellular connections at the surgical site.

2. The technique according to claim 1, wherein the step of vibrating said tumescent solution in the ultrasonic range includes the step of passing ultrasonic vibrations through a skin layer proximate to said surgical site.

3. The technique according to claim 2, wherein the step of injecting a quantity of tumescent solution includes the step of infusing said tumescent solution using an infusion pump.

4. The technique according to claim 2, further including the step of administering, via said tumescent solution, antibiotics.

5. A technique for disrupting connective tissue in fat comprising the steps of:
    a) depositing a quantity of tumescent solution proximate to a selected tissue site;
    b) vibrating said selected tissue site in the ultrasonic range using externally applied ultrasonic vibrations.

6. The technique according to claim 5, wherein the step of vibrating said selected tissue site in the ultrasonic range includes the step of passing ultrasonic vibrations through a skin layer proximate to said selected tissue site.

7. The technique according to claim 6, wherein the step of vibrating said selected tissue site is conducted for a period sufficient to damage intercellular connections at said selected tissue site.

8. The technique according to claim 7, further including the step of administering, via said quantity of tumescent solution, antibiotics to said selected tissue site.

9. A surgical technique comprising the steps of:
    a) injecting a quantity of tumescent solution into a surgical site;
    b) via vibrations of a skin layer, ultrasonically vibrating said surgical site and said tumescent solution for a period sufficient to damage connections at said surgical site.

10. The surgical technique according to claim 9, wherein the steps of injecting and ultrasonically vibrating are performed simultaneously.

11. The surgical technique according to claim 9, wherein the step of ultrasonically vibrating includes the step of passing ultrasonic vibrations through skin proximate to said surgical site.

12. The surgical technique according to claim 9, further including the step of administering, via said tumescent solution, antibiotics.

\* \* \* \* \*